United States Patent
Tapalian et al.

(10) Patent No.: US 6,507,684 B2
(45) Date of Patent: Jan. 14, 2003

(54) OPTICAL MICROCAVITY RESONATOR SYSTEM

(75) Inventors: Haig Charles Tapalian, Canton, MA (US); Juha-Pekka Laine, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 09/893,954

(22) Filed: Jun. 28, 2001

(65) Prior Publication Data

US 2002/0114563 A1 Aug. 22, 2002

Related U.S. Application Data

(60) Provisional application No. 60/214,383, filed on Jun. 28, 2000.

(51) Int. Cl.⁷ .................................................. G02B 6/26
(52) U.S. Cl. ............................. 385/30; 385/28; 385/33; 385/35
(58) Field of Search ............................. 385/30, 27, 28, 385/29, 33, 39, 14, 42–50, 31, 32, 35; 372/6, 9

(56) References Cited

U.S. PATENT DOCUMENTS

| | | | |
|---|---|---|---|
| 4,695,121 A | 9/1987 | Mahapatra et al. | 385/14 |
| 4,807,232 A | 2/1989 | Hart et al. | 372/18 |
| 5,130,843 A | 7/1992 | He et al. | 359/285 |
| 5,268,693 A | 12/1993 | Walsh | 372/74 |
| 5,420,688 A | 5/1995 | Farah | 356/358 |
| 5,742,633 A | 4/1998 | Stone et al. | 372/92 |
| 6,009,115 A * | 12/1999 | Ho | 385/50 X |
| 6,023,540 A | 2/2000 | Walt et al. | 385/12 |
| 6,040,191 A | 3/2000 | Grow | 436/172 |
| 6,058,127 A | 5/2000 | Joannopoulos et al. | 372/92 |
| 6,266,459 B1 | 7/2001 | Walt et al. | 385/12 |
| 6,389,197 B1 * | 5/2002 | Iltchenko et al. | 385/28 |

OTHER PUBLICATIONS

Laine, J. P. et al., Silica microsphere resonator and SPARROW waveguide coupler structures, Integrated Photonics Research 2000, OSA Technical Digest, Quebec City, Canada, Jul. 2000.

Laine, J. P. et al., Microsphere resonator mode characterization by pedestal anti–resonant Reflecting waveguide coupler, IEEE Photonics Technology Letters, vol. 12, 1004–1006, 2000.

Little, B. et al., Pedestal antiresonant Reflecting waveguides for robust coupling to microsphere resonators and for microphotonics circuits, Optics Letters, vol. 25, No. 1, pp. 73–75, 2000.

Laine, J. P. et al., Novel techniques for whispering–gallery–mode excitation in silica microspheres, Integrated Photonics Research 1999, OSA Technical Digest, Santa Barbara, California, Jul. 1999.

\* cited by examiner

Primary Examiner—Phan T. H. Palmer
(74) Attorney, Agent, or Firm—McDermott, Will & Emery

(57) ABSTRACT

An optical resonator system includes a substrate, and a SPARROW optical waveguide disposed on the substrate for evanescently coupling light into an optical microcavity. The SPARROW waveguide includes a multi-layer dielectric stack formed of alternating high and low refractive index dielectric layers, and a waveguide core disposed on the dielectric stack. The waveguide core has an input end and an output end, and is adapted for transmitting optical radiation incident on the input end to the output end. The optical microcavity is disposed at a distance from the optical waveguide that is sufficiently small so as to allow evanescent coupling of light from the optical waveguide into the optical microcavity. The dielectric stack in the SPARROW waveguide isolates the waveguide core and the microcavity from the substrate, so that an optical coupling efficiency approaching 100% can be obtained.

28 Claims, 8 Drawing Sheets

OPTICAL MICROCAVITY RESONATOR SYSTEM

CROSS-REFERENCE TO RELATED APPLICATIONS

This application claims the benefit of priority from U.S. provisional patent application Ser. No. 60/214,383, filed Jun. 28, 2000, entitled Micro-Optic Resonator Readout.

STATEMENT REGARDING FEDERALLY SPONSORED RESEARCH

Not Applicable

REFERENCE TO MICROFICHE APPENDIX

Not Applicable

FIELD OF THE INVENTION

The present invention relates to optical microcavity resonators, and in particular to highly efficient, low-loss optical microcavity resonators having relatively high quality factors (Q's).

BACKGROUND OF THE INVENTION

During the past few years, a substantial amount of research has been performed in the field of optical microcavity physics, in order to develop high cavity-Q optical microcavity resonators. In general, resonant cavities that can store and recirculate electromagnetic energy at optical frequencies have many useful applications, including high-precision spectroscopy, signal processing, sensing, and filtering. Many difficulties present themselves when conventional planar technology, i.e. etching, is used in order to fabricate high quality optical resonators, because the surfaces must show deviations of less than about a few nanometers. Optical microsphere resonators, on the other hand, can have quality factors that are several orders of magnitude better than typical surface etched resonators, because these microcavities can be shaped by natural surface tension forces during a liquid state fabrication. The result is a clean, smooth silica surface with low optical loss and negligible scattering. These microcavities are inexpensive, simple to fabricate, and are compatible with integrated optics.

Optical microcavity resonators have quality factors (Qs) that are higher by several orders of magnitude, as compared to other electromagnetic devices. Measured Qs as large at $10^{10}$ have been reported, whereas commercially available devices typically have Qs ranging from about $10^5$ to about $10^7$. The high-Q resonances encountered in these microcavities are due to optical whispering-gallery-modes (WGM) that are supported within the microcavities.

As a result of their small size and high cavity Q, interest has recently grown in potential applications of microcavities to fields such as electro-optics, microlaser development, measurement science, and spectroscopy. By making use of these high Q values, microspheric cavities have the potential to provide unprecedented performance in numerous applications. For example, these microspheric cavities may be useful in applications that call for ultra-narrow linewidths, long energy decay times, large energy densities, and fine sensing of environmental changes, to cite just a few examples.

In order for the potential of microcavity-based devices to be realized, it is necessary to couple light selectively and efficiently into the microspheres. Since the ultra-high Q values of microcavities are the result of energy that is tightly bound inside the cavity, optical energy must be coupled in and out of the high Q cavities, without negatively affecting the Q. Further, the stable integration of the microcavities with the input and output light coupling media should be achieved. Also, controlling the excitation of resonant modes within these microcavities is necessary for proper device performance, but presents a challenge for conventional waveguides.

In general, the desirable characteristics of a microcavity coupler include: 1) efficient WGM excitation; 2) easy alignment of the microcavity with respect to a coupler; 3) clearly defined ports; 4) a robust and integrable structure; and 5) a consistent and inexpensive fabrication process. One of the most efficient prior art methods incorporates phase-matched evanescent wave coupling. One commonly used approach for phase-matched evanescent wave coupling is to polish down the cladding of an optical fiber, until the evanescent field is locally exposed. Other techniques have been used in the prior art for coupling light into the microspheres, for example the prism coupler, and the tapered fiber coupler. For the tapered coupler, a tapered fiber is formed, i.e. a narrow waist is formed on a fiber by heating and gradual stretching.

While the above-mentioned techniques provide efficient coupling, these approaches suffer from a number of drawbacks. For example, most currently existing techniques for the excitation of whispering-gallery-mode (WGM) resonances in optical microcavities are not easily scalable for mass production. Also, the existing techniques are not robust or versatile enough for desired measurement environments. The fabrication of both the exposed fiber and the tapered fiber is nontrivial and intricate, and the resulting couplers are rather fragile. In particular, the tapered fiber coupler requires delicately drawn fibers, less than 5 micrometers in diameter and suspended in air. Also, the prism coupler does not provide guided wave control. Further, the prism coupler uses bulk components, and is therefore less desirable for applications that call for robustness.

Typically, good overall performance is gained by accessing the evanescent field in a waveguide. Also, only waveguide structures provide easy alignment and discrete, clearly defined ports. Leakage from the sphere WGMs onto the fiber cladding modes lowers the coupling efficiency, however. High-Q microcavities are typically composed of high-purity silica, a material whose low refractive index value is commonly used for the cladding of planar fiberoptic waveguides. As a result, a silica sphere coupled to a conventional surface waveguide will lose most of its energy to substrate and cladding radiation. This loss spoils the Q, and reduces the device efficiency. Because of cavity and waveguide mode leakage into the substrate and into the modes within the fiber cladding, power extraction from the input optical radiation is inefficient.

There is a need for a robust and efficient system for coupling light into high Q optical microcavities, so that the high Q values can be fully utilized.

SUMMARY OF THE INVENTION

A method and system is presented for efficiently and robustly coupling optical radiation into an optical microcavity resonator so as to excite resonance modes within the microcavity. In particular, high-Q optical microspheric cavity resonators are evanescently coupled to an optical waveguide chip that has a SPARROW (Stripline Pedestal Anti-Resonant Reflective Optical Waveguide) structure.

When the frequency of the light propagating along the waveguide matches a resonant whispering gallery mode (WGM) of the microspheric cavity, light is coupled into the microsphere. Coupling efficiencies of over 98% may be attained.

The present invention features a low-loss, high-Q optical resonator system. The optical resonator system includes a substrate, an optical waveguide, and an optical microcavity, all integrated into a single structure. The substrate is preferably substantially planar, and may be made of silicon, by way of example. The optical waveguide includes a multilayer dielectric stack disposed on the substrate. The dielectric stack includes alternating high and low refractive index dielectric layers. A waveguide core is disposed on top of the dielectric stack. The waveguide core has an input end and an output end. The waveguide core is adapted for transmitting optical radiation incident on the input end to the output end.

The optical microcavity is constructed and arranged so as to optically interact with optical radiation propagating through the optical waveguide. The optical microcavity may be a microdisk, a microsphere, or a microring, by way of example. In one embodiment, the optical microcavity may be fabricated by melting a tip of a silica optical fiber or wire. The optical microcavity may be substantially spherical in shape, and characterized by a diameter of about 50 micrometers to about 500 micrometers.

Because of the alternating high- and low- index dielectric layers, the reflectivity of the dielectric stack is very high. In particular, the reflectivity of the dielectric stack is high enough to isolate the optical modes in the microcavity and in the waveguide core from the substrate. The maximum distance between the optical microcavity and the optical waveguide is sufficiently small so as to allow evanescent coupling of light from the waveguide into the microcavity, namely the maximum distance is of the order of the wavelength of the light incident upon the waveguide.

DETAILED DESCRIPTION

The present invention provides a robust and efficient integrated-optics system for coupling optical signals into microcavity resonators so as to excite, control and monitor the resonant modes in the microcavity. In particular, the present invention features the evanescent coupling of laser light into optical microcavity resonators, using anti-resonant reflective optical waveguide structures.

Figure 1:
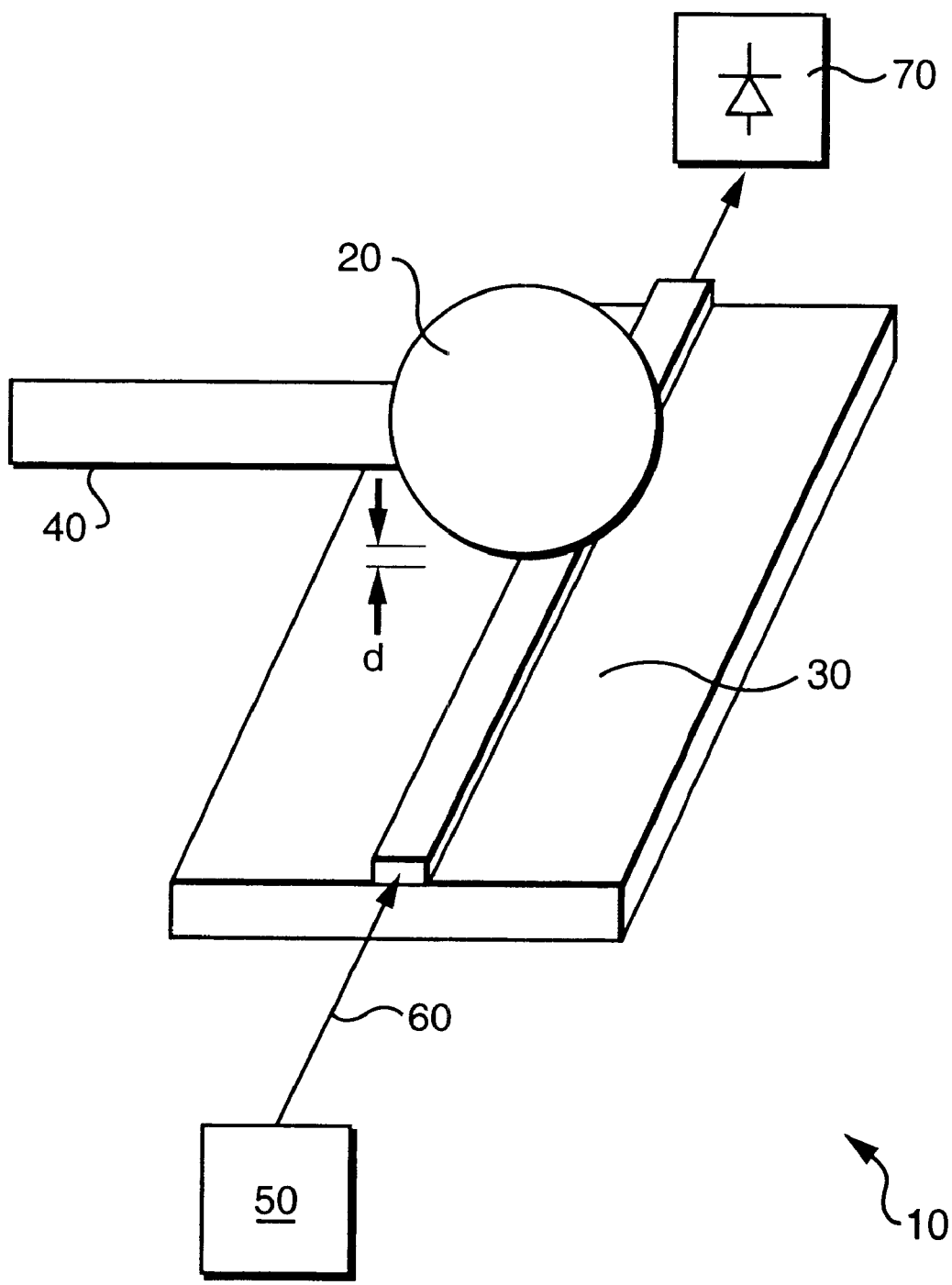
FIG. 1 is a schematic diagram of the elements forming an integrated optical system for coupling laser light onto an optical microcavity resonator, constructed in accordance with the present invention.

FIG. 1 illustrates the elements forming an integrated optical resonator system 10 for evanescently coupling light into an optical microcavity, constructed in accordance with the present invention. In overview, the system 10 includes an optical microcavity 20, and a waveguide chip 30 that is used to couple light into and out of the optical microcavity 20. In the illustrated embodiment, integration of the microcavity 20 and the waveguide chip 30 is accomplished using a fiber stem 40, which remains attached to the optical microcavity 20, following the fabrication of the microsphere. An optical source 50, preferably a laser, provides a beam 60 of input radiation directed to the waveguide. A photodetector 70 detects optical radiation transmitted through the waveguide 30.

Figure 2:
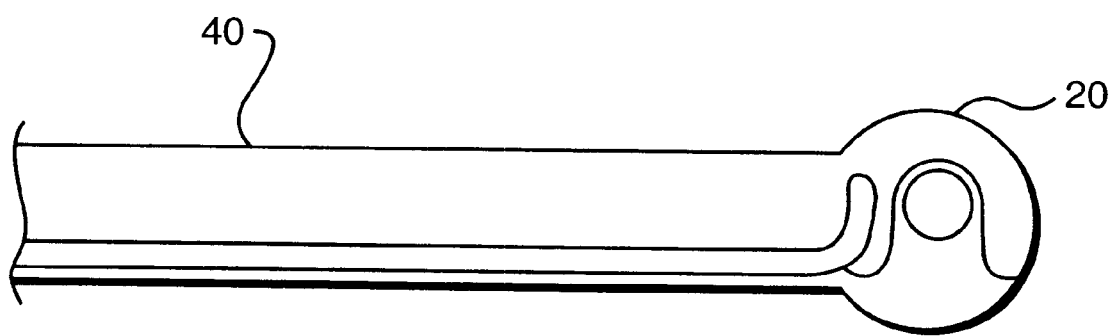
FIG. 2 illustrates an optical microcavity resonator, constructed in accordance with the present invention.

FIG. 2 illustrates in more detail the optical microcavity 20, constructed in accordance with the present invention. Optical microcavities are small spherical particles, disks, or rings, having dimensions of the order of microns to millimeters. In the illustrated embodiment of the invention, the optical microcavity 20 is a substantially spherical particle, typically made of silica. In a preferred embodiment, the optical microcavity 20 is fabricated by surface tension shaping of the tip of freshly melted optical fiber. Melting of the tip of a silica wire or fiber may be accomplished through arcing in a fusion splicer, by means of a gas flame, or using a high-power laser (such as a $CO_2$ laser) to heat the glass. Microspheres, with diameters typically ranging from about 50 micrometers to about 500 micrometers, are obtained by this method. In the illustrated embodiment, the optical microcavity 20 has a diameter of about 200 micrometers, although other sizes are also within the scope of the present invention. In a preferred embodiment, the fiber stem 40 may be left attached to the microcavity, and used for maneuvering the microcavity relative to the optical waveguide.

The most practical and versatile electro-optical coupling mechanisms which could be utilized for microcavity integration are planar waveguide structures. As explained earlier, waveguide structures provide for easy alignment of the microcavity with respect to the coupler, and discrete, clearly defined ports. Also, WGMs in microcavities can be efficiently excited using waveguides.

In particular, it is desirable to implement wafer-based, planar optical waveguides, such as those used for integrated optics. These solid, optical chip structures provide robustness and rigidity, along with the capability of integrated optical system to be fabricated consistently and inexpensively. Prior efforts at implementing a basic integrated-optics coupler configuration using a microcavity and a conventional integrated-optics waveguide made of silica were frustrated, however, because of the difficulty of finding suitable cladding material for the integrated-optics waveguides. The silica waveguide would have to be clad with a material having an index of refraction that is much lower than the index of refraction of silica, in order to avoid leakage of incoming radiation into the cladding radiation modes. Materials having an index of refraction much lower than the index of refraction of silica are not readily available, however, so the above-described waveguide coupling scheme was frustrated.

Figure 3A:
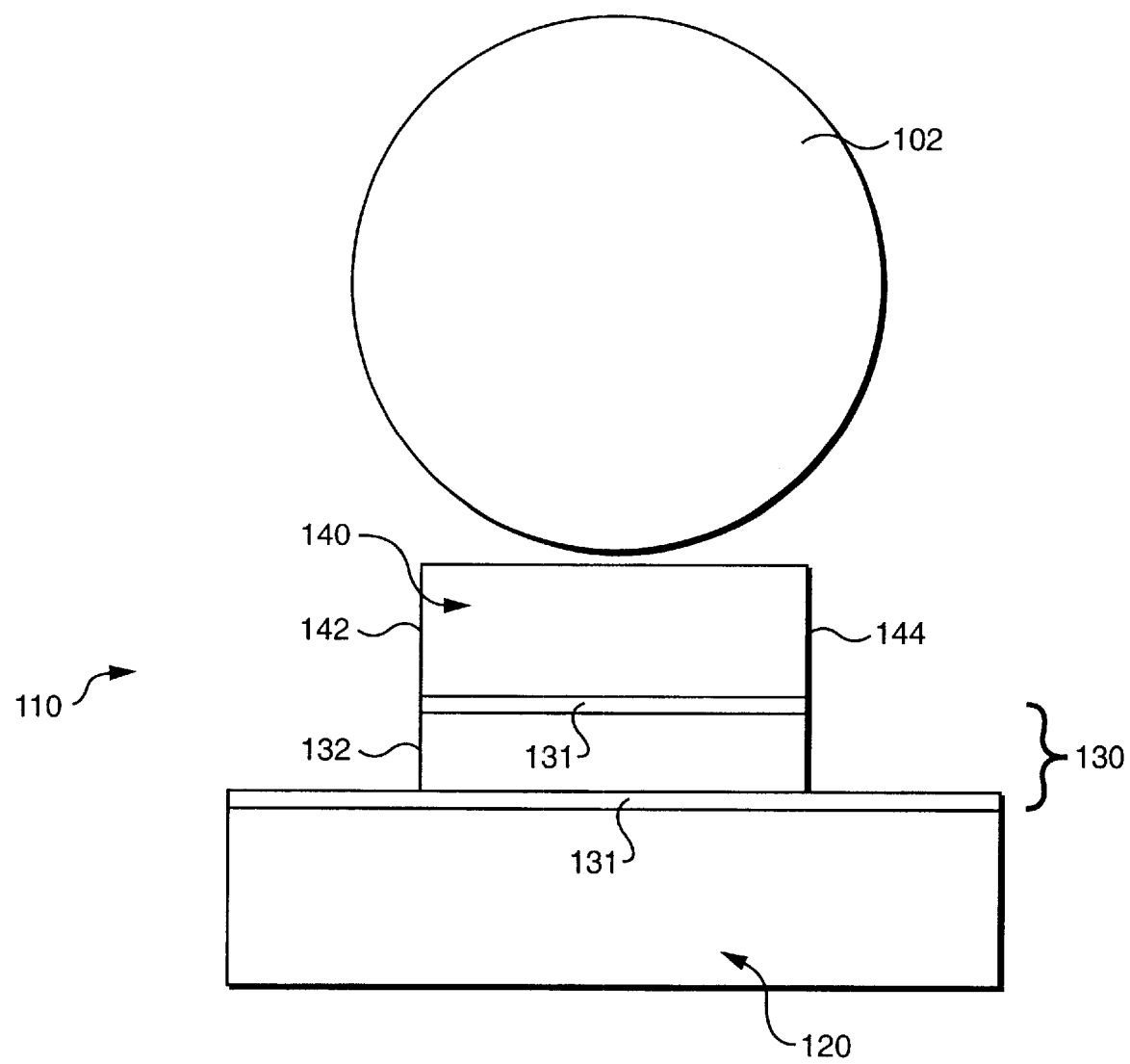
FIG. 3A illustrates a SPARROW optical waveguide, constructed in accordance with the present invention.

In the present invention, a SPARROW (stripline pedestal anti-resonant reflective optical waveguide) integrated-optics waveguide is implemented, in order to overcome the disadvantages mentioned above. FIG. 3A illustrates a SPARROW optical waveguide 110, constructed in accordance with the present invention. The SPARROW waveguide 110 provides an efficient and robust coupling mechanism for exciting whispering-gallery-modes in an optical microcavity 102. The SPARROW 110 includes a multi-layer, high-reflectivity dielectric stack 130 disposed on the substrate 120, and a waveguide core 140. The substrate 120 is substantially planar, and in one embodiment is made of silicon.

The dielectric stack 130 is composed of alternating high ($n_H$) and low ($n_L$) refractive index layers 131 and 132, made of a dielectric material. As a result, the dielectric stack 130 functions as a high reflectivity dielectric mirror. The larger the number of layers 131 and 132, the higher the reflectivity of the stack 130 becomes. While the illustrated embodiment includes only one low index layer 132 disposed between two high index layers 131, the number of the layers 131 and 132 can be increased in order to increase the reflectivity of the stack 130. The alternating layers 131 and 132 forming the dielectric stack 130 provide a cladding for the SPARROW waveguide core 140, i.e. the layers forming the stack 130 may be regarded as cladding layers.

The high reflectivity of the dielectric stack 130 permits isolation of the optical modes of the microcavity 102 and the waveguide core 140 from the waveguide cladding and the substrate. By isolating the waveguide core 140 using the high-reflectivity dielectric stack 130, the SPARROW 110 circumvents the need for obtaining low refractive index cladding materials. As shown in FIG. 3A, one of the high refractive index layers 131 is in contact with the substrate 120.

In one embodiment, the high refractive index layer 131 is made of Si (silicon), while the low refractive index layer 132 is made of $SiO_2$ (silica). In one embodiment, the high refractive index $n_H$ is about 3.5, and the low refractive index $n_L$ is about 1.45, although other refractive indices are also within the scope of the present invention. The refractive indices required for efficiently guiding light within the waveguide depend on the wavelength of optical radiation.

The waveguide core 140 is disposed on top of the dielectric stack 130, and is in contact with another one of the high refractive index layers 131. The waveguide core 140 includes an input end 142 and an output end 144, and is adapted for transmitting optical radiation incident on the input end 142 to the output end 144. In one embodiment, the waveguide core is made of silica, and is characterized by the low refractive index $n_L$.

Figure 3B:
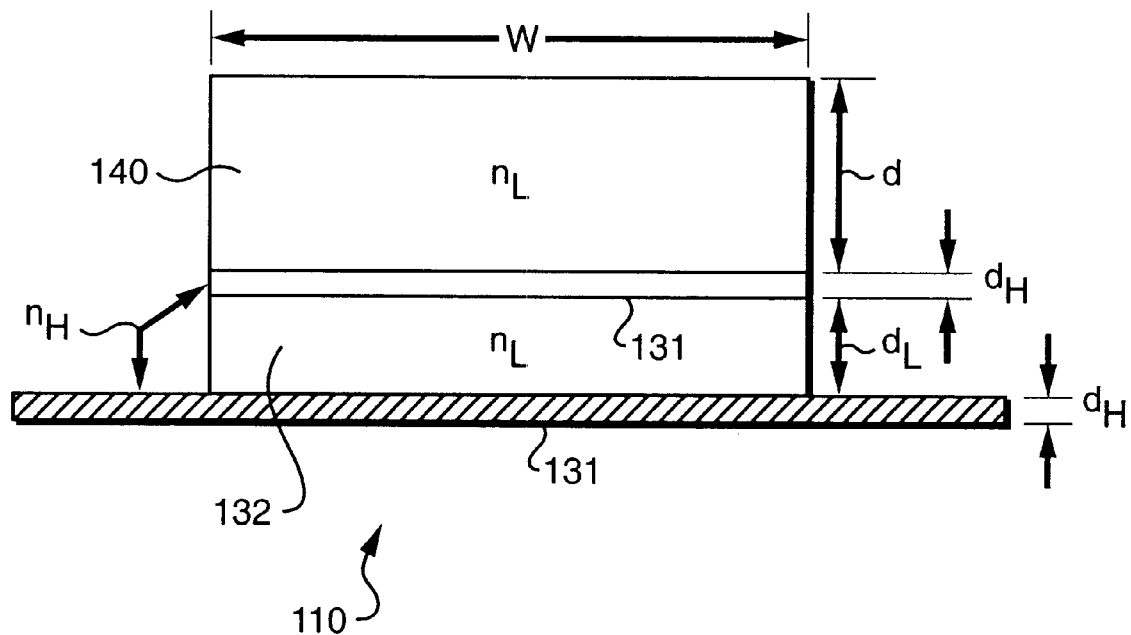
FIG. 3B illustrates a cross-sectional geometry of a SPARROW optical waveguide.

FIG. 3B illustrates a cross-sectional geometry of the SPARROW optical waveguide 110. In FIG. 3B, the low refractive index layer 132 is shown as having a thickness $d_L$ and a refractive index $n_L$, and the high refractive index layer 131 is shown as having a thickness $d_H$ and a refractive index $dn_H$. The waveguide core 140 in FIG. 3B is shown as having a thickness d and a width W, which are preferably selected to provide an effective index $N_L$ for the core 140 that is compatible with the excitation of resonance WGMs in the silica microcavity.

In a preferred embodiment, the thicknesses $d_L$ and $d_H$ of the layers 131 and 132 are chosen to equal one quarter of the guided-light wavelength. In an embodiment of the invention having a geometry illustrated in FIG. 3B, and with given values for $n_H$, $n_L$, and a desired operating wavelength $\lambda_o$ (i.e., the wavelength that matches a WGM resonance within the optical microcavity), the values of $d_L$ and $d_H$ can be computed numerically so as to be equal to one fourth of the guided light wavelength. In one embodiment, the following values were chosen: high refractive index $n_H$=3.5; low refractive index $n_L$=1.45; waveguide core width W=6.0 micrometers; waveguide core thickness d=2.0 micrometers; operating wavelength $\lambda_o$=1.55 micrometers. For these values, the numerically computed effective refractive index $n_L$ for the waveguide core is $n_L$=1.4026. In this embodiment of the invention, the numerically computed thicknesses of the layers 131 and 132 are: $d_L$=1.12 micrometers; $d_H$=120 nanometers. Other embodiments of the invention may have different values of $n_H$, $n_L$, $d_L$, $d_H$, W, and d.

Figure 4:
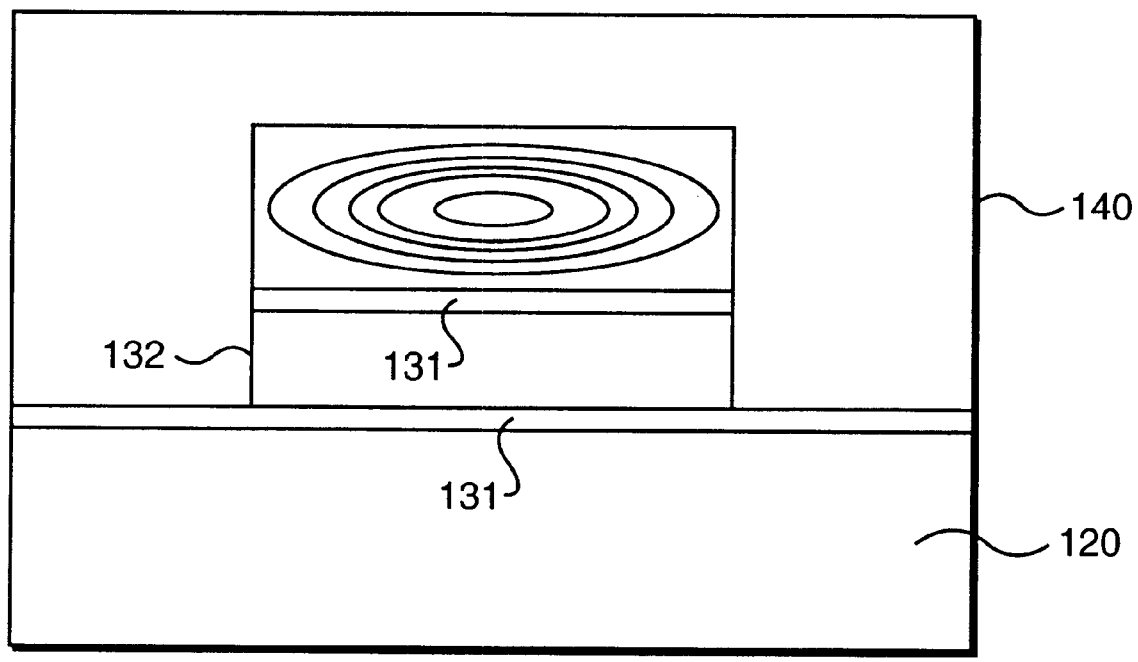
FIG. 4 illustrates a numerically simulated field profile of a SPARROW optical mode.

FIG. 4 illustrates a numerically simulated field profile of a SPARROW optical mode. As seen from FIG. 4, the SPARROW optical mode field is essentially entirely contained within the waveguide core 140 on top of the dielectric stack 130, and is isolated from the substrate 120. The successful elimination of both the sphere mode and the waveguide mode leakage into the substrate 120, as illustrated in FIG. 4, results in extremely high coupling efficiencies.

Figure 5B:
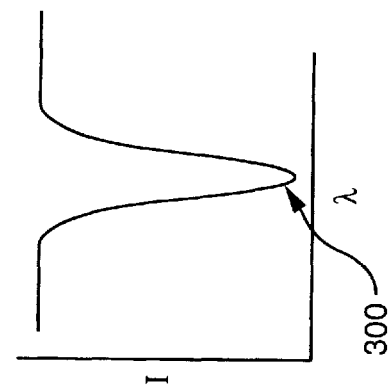
FIG. 5B illustrates the intensity of the optical radiation transmitted through the SPARROW waveguide illustrated in FIG. 5A when the input light wavelength is scanned across a WGM resonance.
Figure 5A:
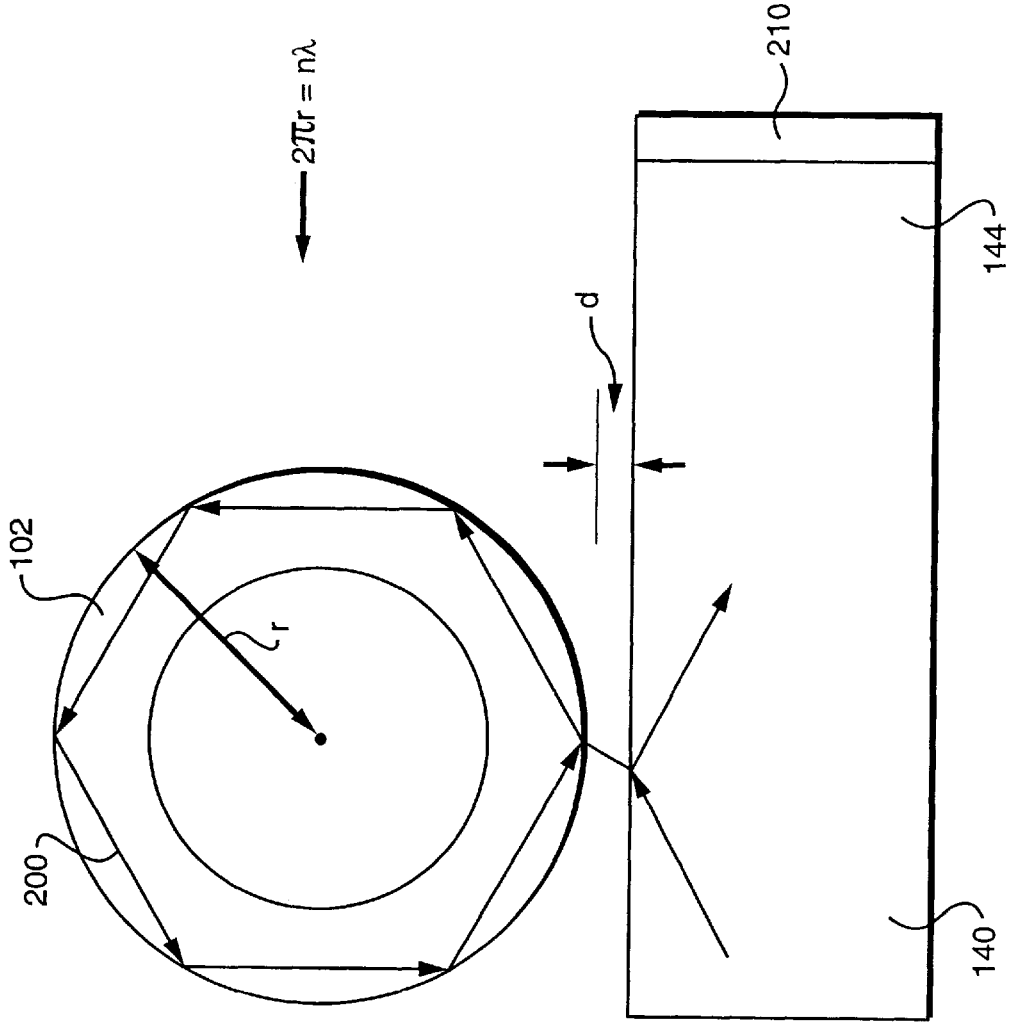
FIG. 5A illustrates evanescent coupling of optical radiation from a SPARROW optical waveguide onto a WGM resonance mode supported within a ring-shaped optical microcavity resonator.

FIGS. 5A illustrates evanescent coupling of optical radiation from the SPARROW optical waveguide onto a WGM resonance 200 supported within a ring-shaped optical microcavity 102. An evanescent wave appears whenever a light wave undergoes total internal reflection at a dielectric interface, such as the interface between the silica waveguide 140 and the surrounding air. As shown in FIG. 5A, the waveguide 140 has a higher index of refraction, as compared to the surrounding air. The evanescent portion of the waveguide mode field is the exponentially decaying portion of the waveguide mode field, outside the relatively high index region of the waveguide. The evanescent wave decays exponentially with the distance from the surface of the waveguide core on a length scale of the order of the optical wavelength.

The coupling gap d between the microcavity 102 and the waveguide 140 is selected to be within the range for evanescent coupling between the waveguide 140 and the microcavity 102, i.e. of the order of one wavelength of the optical mode propagating in the waveguide. With this configuration, evanescent coupling occurs between the waveguide 140 and the microcavity 102 when the wavelength of the evanescent field of the waveguide mode field matches the wavelength of a resonant WGM 200 supported within the microcavity 102. In resonant WGMs, light is trapped near the surface of the microcavity by repeated total internal reflections, and travels in a circle around the microcavity near the surface of the microcavity, as illustrated in FIG. 5A. The wavelengths of the resonant WGMs are thus determined approximately by the radius r of the microcavity 102, i.e. WGM resonances occur at wavelengths given by:

$$2\pi r = n \lambda.$$

When WGM resonances are excited in the microcavity 102, light continues to circulate just inside the surface of the microcavity, with virtually no loss except for residual absorption and scattering in the dielectric. This is why extremely high Q-factors, up to over $10^{10}$, can be achieved in these dielectric microcavities. In practice, the shapes which are obtained for the optical microcavity 120 are not perfectly spherical. As a consequence, many different radial and polar cavity modes may be observed within the fine-tuning wavelength modulation cycle of the incident light. Each mode possesses a different linewidth and thus a different cavity Q.

The intensity of the light transmitted through the waveguide 140 is detected by a photodetector 210 positioned at an output end 144 of the waveguide, as shown in FIG. 5A. The photodetector output is illustrated in FIG. 5B. When evanescent light just outside the surface of the waveguide 140 is coupled onto the microcavity 120 and a WGM resonance is excited within the microcavity, the intensity of the optical radiation transmitted through the waveguide can approach zero at the wavelength of the resonance, implying near 100% coupling efficiency, as shown in FIG. 5B. Because light at the resonance wavelength is coupled into the microcavity resonator, a resonance dip 300 occurs in the transmitted intensity. The cavity Q factor for the microcavity can be determined by the linewidth of the resonance mode: the narrower the linewidth, the higher the cavity Q. Linewidth is also affected by other parameters such as surface quality, bending losses, and scattering effects, all of which contribute to the cavity Q.

Figure 6:
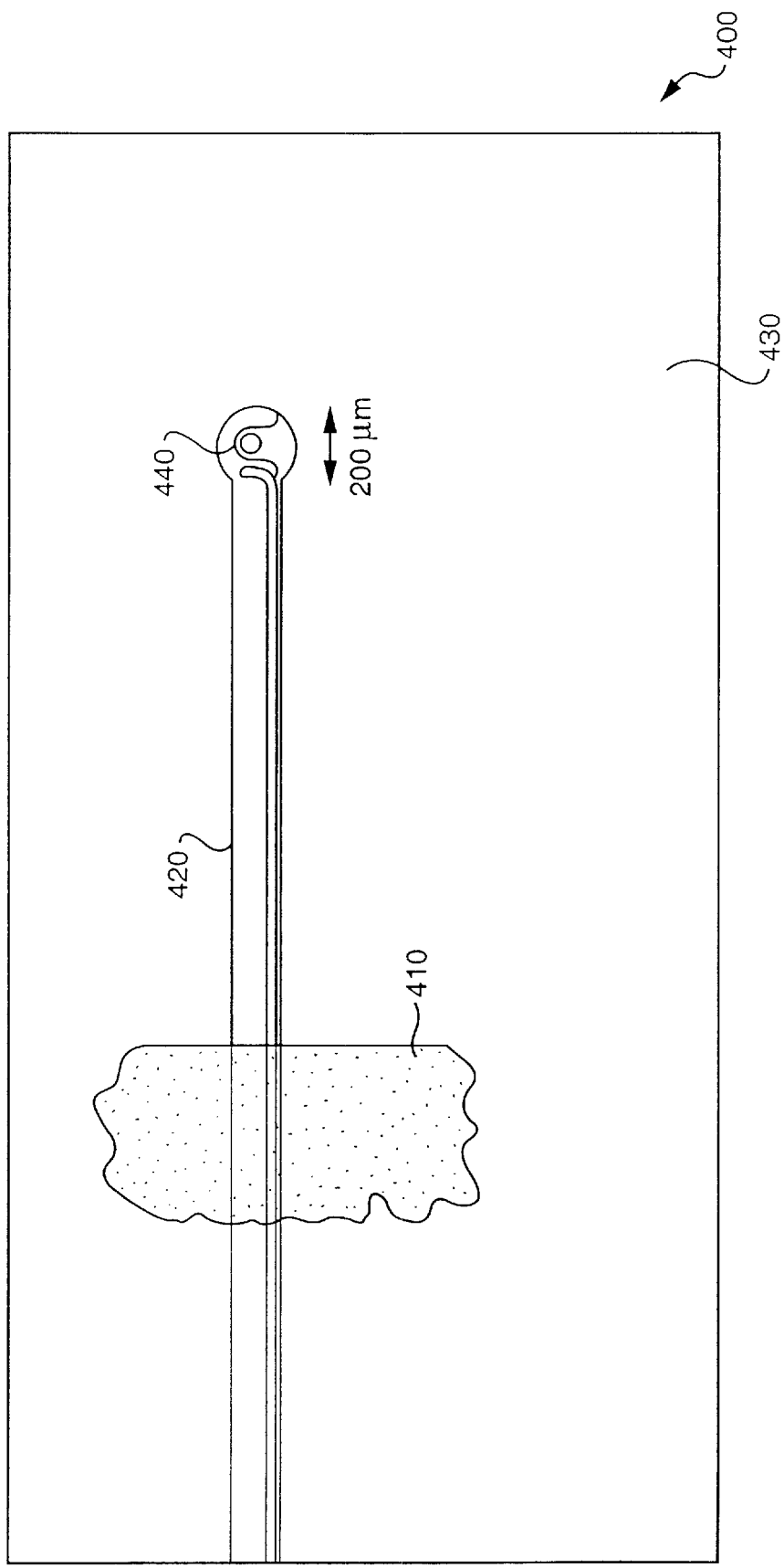
FIG. 6 illustrates an integrated microcavity/waveguide structure.

A primary advantage of the SPARROW waveguide is that it facilitates the integration of high-Q microsphere cavities onto wafer-based optical circuits. An integrated microcavity/ waveguide structure 400 is illustrated in FIG. 6. Bonding agents such as epoxy 410 can be used to attach the fiber stem 420 to the waveguide chip 430. The key factors which determine the success of this integration technique are the system parameter sizes (fiber stem diameter and length, and microcavity diameter). When standard fiber (125 $\mu$m cladding diameter) is utilized as the fiber stem, there is sufficient stiffness to support an average-size microcavity (~250 $\mu$m diameter). In the illustrated embodiment of the invention, a fiber stem 420 approximately 125 $\mu$m in diameter and a microcavity 440 approximately 200 $\mu$m in diameter are integrated with a waveguide.

Figure 7:
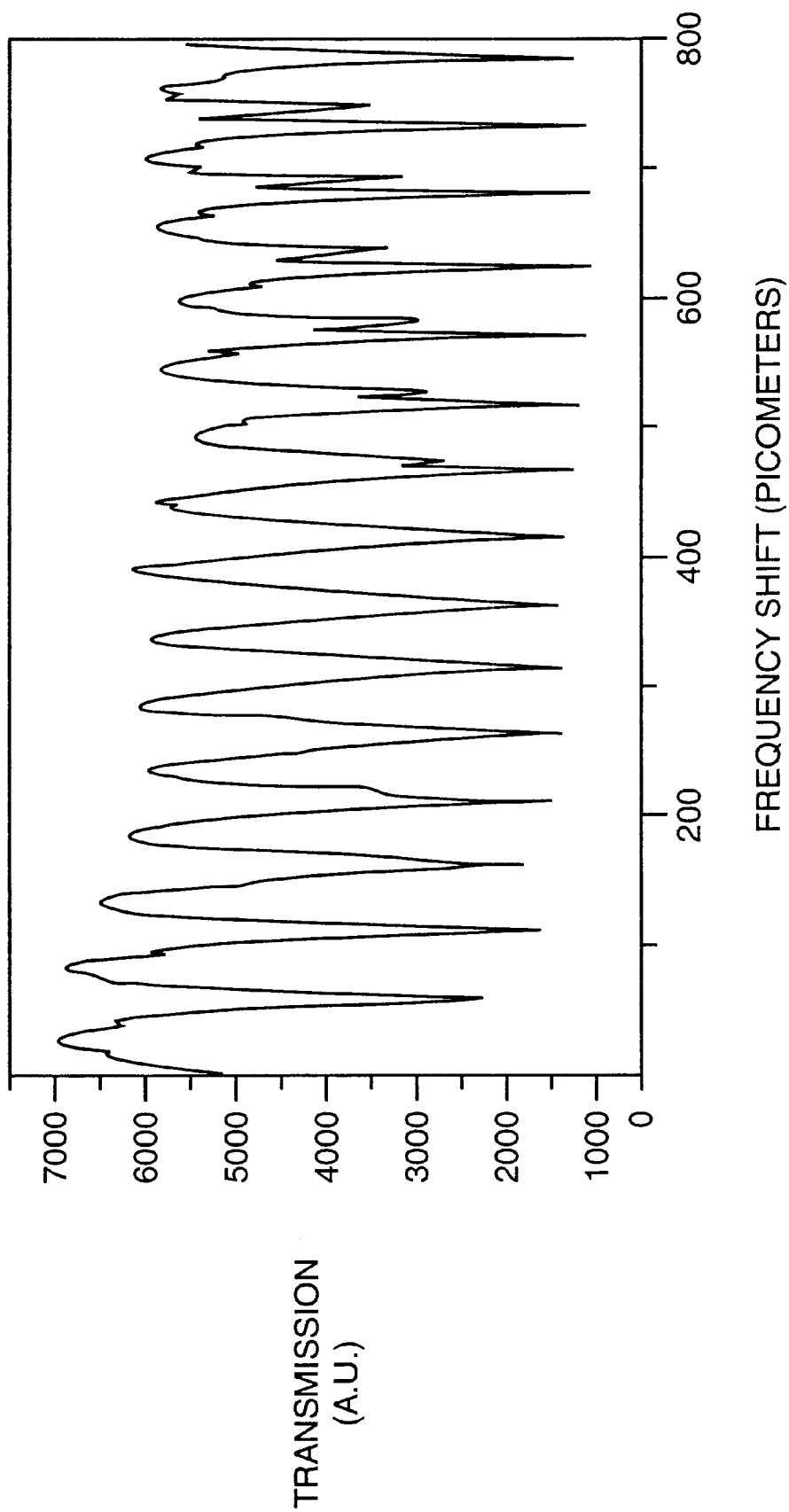
FIG. 7 illustrates the waveguide transmission response of an optical microcavity coupled to a SPARROW waveguide when the input light wavelength is scanned across multiple WGM resonances.

The SPARROW waveguide is characterized by a power extraction efficiency unmatched by any other prior art methods of coupling light onto microcavity resonators, up to over 99%. FIG. 7 illustrates a waveguide transmission response of a microcavity coupled to a SPARROW waveguide. The transmission spectrum is shown near a central resonance wavelength of about 1.55 $\mu$m. Resonant dips can be observed in the spectrum as the microcavity extracts power from the waveguide. The transmitted power levels in the absence of the microcavity remain within approximately 5% of the peak values observed in FIG. 7. An extraction efficiency greater than 85% is seen from FIG. 7, however, extraction efficiencies over 98% have also been observed.

SPARROW couplers also provide the advantages that result from lithographic fabrication. These advantages include the precise control of component parameters, and the ease of large scale and/or batch mode fabrication. The components of the SPARROW waveguide may be fabricated using: 1) thermal oxidation of a silicon wafer; 2) low-pressure chemical vapor deposition; and 3) reactive ion etching. In one embodiment, the fabrication process for the SPARROW waveguide 110 is designed to minimize leakage loss at the operating wavelength of 1.55 $\mu$m. In this embodiment, the fabrication process begins with 1.7 $\mu$m of thermal oxidation on a 4 inch wafer of silicon. This process is followed by a 120 nm layer of amorphous silicon deposited at 560° C. by LPCVD (low pressure chemical vapor deposition). Finally, 2.0 $\mu$m of silica is grown to form the core layer. The stack is then patterned by reactive-ion etching to form the SPARROW structure. The first 1–2 $\mu$m of etching may be performed with a wet-etch step in order to generate smoother core sidewalls.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An optical resonator system, comprising:
   A. a substrate;
   B. an optical waveguide, comprising:
      (a) a multi-layer dielectric stack disposed on said substrate, said dielectric stack including alternating high and low refractive index dielectric layers;
      (b) a waveguide core disposed on said dielectric stack and having an input end and an output end, said waveguide core being adapted for transmitting optical radiation incident on said input end to said output end, said waveguide core being in contact with one of said high refractive index layers; and
   C. an optical microcavity constructed and arranged so as to optically interact with said optical radiation incident on said input end of said optical waveguide core.

2. An optical resonator system according to claim 1, wherein said optical microcavity is disposed at a distance from said optical waveguide that is sufficiently small so as to allow evanescent coupling between said microcavity and said optical waveguide.

3. An optical resonator system according to claim 2, wherein said evanescent field is characterized by at least one frequency substantially dual to at least one resonant mode of said optical microcavity.

4. An optical resonator system according to claim 3, wherein at least one of said resonant modes of said optical microcavity is a whispering gallery mode.

5. An optical resonator system according to claim 4, wherein said optical microcavity has a substantially spherical shape, and wherein the wavelengths of the whispering gallery modes of said microcavity are substantially equal to related to $\lambda$, $\lambda$ being related to the radius r and the degree of sphericity of said substantially spherical microcavity by the formula:

$$2\pi r = n\lambda,$$

where n is a nonzero integer.

6. An optical resonator system according to claim 2, wherein said distance is less than one wavelength of said optical radiation propagating through said optical waveguide.

7. An optical resonator system according to claim 1, wherein the thickness and the width of said waveguide core is chosen so as to provide an effective refractive index for said waveguide core that matches the refractive index of said microcavity when a resonant WGM is excited therewithin.

8. An optical resonator system according to claim 7, wherein said thickness of said waveguide core is chosen to match the wavelength of said optical radiation propagating through said optical waveguide.

9. An optical resonator system according to claim 7, wherein said thickness of said waveguide core is about 2.0 $\mu$m, said width of said waveguide is about 6.0 $\mu$m, and said effective refractive index for said waveguide core is about 1.40.

10. An optical resonator system according to claim 1, wherein said optical microcavity is selected from the group consisting of microspheres, microdisks, and microrings.

11. An optical resonator system according to claim 1, further comprising an optical source for generating a beam of light directed to said input end of said optical waveguide.

12. An optical resonator system according to claim 1, further comprising at least one detector constructed and arranged so as to detect output optical radiation from said output end of said optical waveguide.

13. An optical resonator system according to claim 1, wherein said optical microcavity is made of silica.

14. An optical resonator system according to claim 1, wherein said optical waveguide forms an integrated optical chip.

15. An optical resonator system according to claim 1, wherein said optical waveguide and said optical microcavity form an integrated optical chip.

16. An optical resonator system according to claim 1, wherein the coupling efficiency of said evanescent field into said optical microcavity is from about 10% to about 99.99%.

17. An optical resonator system according to claim 1, wherein the reflectivity of said dielectric stack is sufficient to isolate the optical modes within said waveguide core from said substrate.

18. An optical resonator system according to claim 1, wherein the reflectivity of said dielectric stack is sufficient to isolate the optical modes in said microcavity from said substrate.

19. An optical resonator system according to claim 1, wherein said optical microcavity is fabricated by melting one end of an optical fiber.

20. An optical resonator system according to claim 1, wherein said optical microcavity is characterized by a quality factor (Q) from about $10^5$ to about $10^{10}$.

21. An optical resonator system according to claim 1, wherein said optical microcavity is characterized by a diameter of about 50 $\mu$m to about 500 $\mu$m.

22. An optical resonator system according to claim 1, wherein said optical microcavity is characterizd by a diameter of about 200 $\mu$m.

23. An optical resonator system according to claim 1, wherein one of said low refractive index layers is in contact with said substrate, and one of said high refractive index layers is in contact with said waveguide core.

24. An optical resonator system according to claim 1, wherein said high refractive index is about 3.5, and said low refractive index is about 1.45.

25. An optical resonator system according to claim 1, wherein said optical microcavity has a substantially spherical shape.

26. An optical resonator system according to claim 1, wherein said low index dielectric layer and said waveguide core comprises silica.

27. An optical resonator system according to claim 1, wherein said high index dielectric layer comprises silicon.

28. An optical resonator system according to claim 1, wherein the coupling efficiency of said evanescent field into said optical microcavity is about 99%.

* * * * *